United States Patent
Heide et al.

(10) Patent No.: US 11,712,504 B2
(45) Date of Patent: *Aug. 1, 2023

(54) MEDICAL DEVICE WITH ADDITIVELY APPLIED CONVERTER INCLUDING A CONDUCTIVE PATH

(71) Applicant: Fresenius Medical Care Deutschland GmbH, Bad Homburg (DE)

(72) Inventors: Alexander Heide, Eppstein (DE); Dejan Nikolic, Bad Soden (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 871 days.

This patent is subject to a terminal disclaimer.

(21) Appl. No.: 16/495,530

(22) PCT Filed: Mar. 20, 2018

(86) PCT No.: PCT/EP2018/057011
§ 371 (c)(1),
(2) Date: Sep. 19, 2019

(87) PCT Pub. No.: WO2018/172351
PCT Pub. Date: Sep. 27, 2018

(65) Prior Publication Data
US 2020/0016316 A1    Jan. 16, 2020

(30) Foreign Application Priority Data

Mar. 24, 2017  (DE) .......................... 102017106403.6

(51) Int. Cl.
*A61M 1/36* (2006.01)
*A61M 1/14* (2006.01)
(Continued)

(52) U.S. Cl.
CPC .............. *A61M 1/367* (2013.01); *A61M 1/14* (2013.01); *A61M 1/3413* (2013.01);
(Continued)

(58) Field of Classification Search
CPC ...... A61M 1/367; A61M 1/14; A61M 1/3413; A61M 2205/0233; A61M 2205/0244;
(Continued)

(56) References Cited

U.S. PATENT DOCUMENTS

| | | | |
|---|---|---|---|
| 4,734,184 A | 3/1988 | Burleigh et al. | |
| 7,887,509 B2 | 2/2011 | Thiebaud et al. | |

(Continued)

FOREIGN PATENT DOCUMENTS

| | | |
|---|---|---|
| CN | 101351237 A | 1/2009 |
| CN | 101421601 A | 4/2009 |

(Continued)

OTHER PUBLICATIONS

International Preliminary Report in Application No. PCT/EP2018/057011, dated Sep. 24, 2019, 7 pages (Full English Translation).

(Continued)

*Primary Examiner* — Lauren P Farrar
*Assistant Examiner* — Hamza A Darb
(74) *Attorney, Agent, or Firm* — Fish & Richardson P.C.

(57) ABSTRACT

This disclosure relates to a medical device including, a hard part, a converter, and a conductive path. The hard part has fluid paths for guiding a medical fluid, in particular blood, through the hard part. The converter is arranged to measure a characteristic of the medical fluid while the fluid is present in one of the fluid paths. At least a first section of the converter or of the conductive path is applied to or superimposed on the hard part by a first additive application method. At least a second section of the converter or of the conductive path is applied to the hard part by a second (Continued)

application method. The first and the second additive application methods differ from each other.

20 Claims, 4 Drawing Sheets

(51) Int. Cl.
    *A61M 1/34*     (2006.01)
    *G01N 27/07*     (2006.01)
    *H10N 30/30*     (2023.01)
    *H10N 30/857*     (2023.01)

(52) U.S. Cl.
    CPC ..... *G01N 27/07* (2013.01); *A61M 2205/0233* (2013.01); *A61M 2205/0244* (2013.01); *A61M 2205/0294* (2013.01); *A61M 2205/12* (2013.01); *A61M 2205/3317* (2013.01); *A61M 2205/3334* (2013.01); *A61M 2207/00* (2013.01); *H10N 30/302* (2023.02); *H10N 30/857* (2023.02)

(58) Field of Classification Search
    CPC ...... A61M 2205/0294; A61M 2205/12; A61M 2205/3317; A61M 2205/3334; A61M 2207/00; A61M 2205/0227; A61M 2205/0272; A61M 2205/3379; A61M 2205/70; A61M 1/3663; G01N 27/07; H01L 41/1132; H01L 41/193
    See application file for complete search history.

(56) References Cited

U.S. PATENT DOCUMENTS

| | | | |
|---|---|---|---|
| 9,308,332 | B2 | 4/2016 | Heppe |
| 9,399,089 | B2 | 7/2016 | Nikolic et al. |
| 10,463,306 | B2 | 11/2019 | Maurer et al. |
| 10,507,277 | B2 | 12/2019 | Lauer |
| 2009/0012452 | A1 | 1/2009 | Slepicka et al. |
| 2010/0030167 | A1 | 2/2010 | Thirstrup et al. |
| 2011/0214504 | A1* | 9/2011 | Bradley .................. G01L 19/14 73/723 |
| 2016/0059012 | A1 | 3/2016 | Adamson et al. |
| 2020/0093974 | A1* | 3/2020 | Heide ..................... A61M 1/14 |

FOREIGN PATENT DOCUMENTS

| | | |
|---|---|---|
| CN | 106132296 A | 11/2016 |
| CN | 106255519 A | 12/2016 |
| DE | 102009018664 A1 | 10/2010 |
| DE | 102010024654 A1 | 12/2011 |
| EP | 2559656 A1 | 2/2013 |
| JP | H09-47431 | 2/1997 |
| JP | 2004-512914 | 4/2004 |
| JP | 2010-532217 | 10/2010 |
| JP | 2010-258334 | 11/2010 |
| WO | WO 2002/039086 | 5/2002 |
| WO | 2007/095597 A1 | 8/2007 |
| WO | 2011/113838 A1 | 9/2011 |

OTHER PUBLICATIONS

International Search Report and Written Opinion in Application No. PCT/EP2018/057011, dated May 22, 2018, 8 pages (Full English Translation).

de.wikipedia.org [online], "'Generatives Fertigungsverfahren'—Versionsunterschied," retrieved Nov. 16, 2017, retrieved from URL <https://de.wikipedia.org/w/index.php?title=Generatives_Fertigungsverfahren&oldid=163432044>, 14 pages (with English translation).

* cited by examiner

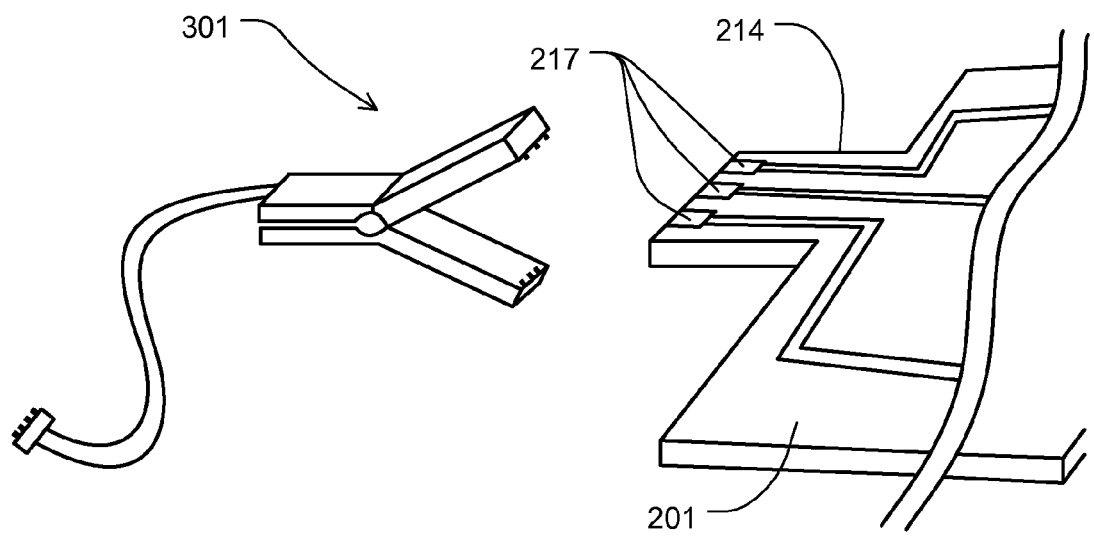
Fig. 5a
Fig. 5b
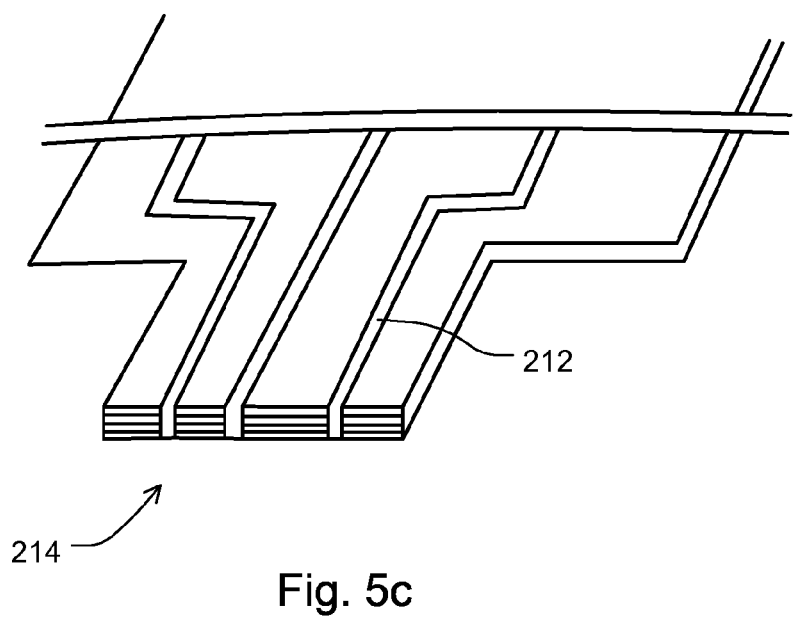
Fig. 5c

MEDICAL DEVICE WITH ADDITIVELY APPLIED CONVERTER INCLUDING A CONDUCTIVE PATH

CROSS-REFERENCE TO RELATED APPLICATIONS

The present application is the national stage entry of International Patent Application No. PCT/EP2018/057011, filed on Mar. 20, 2018, and claims priority to application No. DE 10 2017106 403.6, filed in the Federal Republic of Germany on Mar. 24, 2017, the disclosure of which are expressly incorporated herein in entirety by reference thereto

TECHNICAL FIELD

This disclosure relates to a medical device. It further relates to a production method for a medical device.

BACKGROUND

Blood treatment apparatuses are connectable to at least one medical device for blood treatment. Such a connectable medical device may be a blood cassette, in which blood is treated or temporarily stored. Some of the connectable medical devices are disposable.

SUMMARY

A medical device described herein can have at least one hard part with complete or incomplete fluid paths for conducting a medical fluid, in particular blood, in the hard part or through the hard part.

The medical device further comprises at least one converter. The converter is arranged to measure a characteristic of the medical fluid or of another fluid while the fluid is present in the fluid path. Alternatively or additionally, the converter is arranged to measure a characteristic of the medical device or to measure an effect, for example, of external or internal pressure applied to the medical device.

The converter is at least in one section thereof applied directly or indirectly to the hard part by an additive application method, preferably a printing method.

The medical device further comprises at least one conductive path.

At least a second section of the converter or of the conductive path is applied to the hard part by a second additive application method.

The first and second additive application methods are different from each other.

The method described herein, serves particularly the production of a medical device. It encompasses producing or providing a hard part of the medical device which comprises fluid paths, a fluid system or sections thereof for a medical fluid.

The method further encompasses the application of at least a first section of a converter or of a conductive path to the hard part by a first additive application method, preferably a printing method.

Further, the method described herein encompasses the application of at least a second section of the converter or of the conductive path to the hard part by a second additive application method.

The treatment apparatus described herein comprises at least one multipole connector for the connection with the multipole connecting device of a medical device.

The treatment apparatus may be configured to receive and process the signals received by the multipole connector.

The treatment apparatus may be connected to a medical device.

In all of the embodiments herein, the use of the expression "may be" and "may have" etc. is synonymous to "is preferably" or "has preferably," etc. respectively, and is intended to illustrate an embodiment.

Embodiments described herein may comprise one or several of the aforementioned or following features. In this way, the features mentioned herein may in any combination thereof be subject-matter of the embodiments unless the person skilled in the art recognizes a concrete combination as technically impossible. Furthermore, embodiments are subject-matter of the dependent claims.

Whenever numerical words are herein mentioned, the person skilled in the art will recognize or understand them as indications of numerical lower limits. Unless it leads the person skilled in the art to an evident contradiction, the person skilled in the art will comprehend the specification for example of "one" encompassing "at least one". This understanding is also equally encompassed as the interpretation that a numeric word, for example, "one" may alternatively mean "exactly one", wherever this is evidently technically possible for the person skilled in the art. Both are encompassed and apply herein to all used numerical words.

The information "top" and "bottom" are to be understood, in case of doubt by the person skilled in the art, as absolute or relative spatial information which refer to the position of the respective component during its intended use.

In some exemplary embodiments described herein, the hard part (being herein also denoted as hard body or as substrate), and/or its accessories like tubes, etc., are to be understood as the part which is usually produced by an injection molding process and therefore referred to herein as "hard" body of the medical device, wherein the hard body may be covered by a comparatively "soft" film. The hard part may be made of PP (polypropylene), PE (polyethylene), PA, ABS, PMMA, PC, PVC or of other polymer sufficiently known to the person skilled in the art or of other materials. It may be made of insulator materials, such as in particular, e.g., ceramic.

The terms "sensor" and "sensor arrangement" are used, within the scope of the present description, synonymously for a system comprising or consisting of a converter, signal transmission components and/or evaluation unit. The converter is thereby to be understood preferably as a section of the sensor provided on the device side which is in contact with the measuring medium. The signal transmission components likewise belonging to the sensor arrangement forward the result of their measurement to the evaluation unit, which in the prior art is usually provided on the machine side.

In some embodiments described herein, a "line sequence" in the sense of the present description is to be understood as a local environment with respective specific conditions regarding the material, the topology, the function in the medical device and the spatial extent.

The term "line sequence" may be a sequence of different structures of elements used for conducting. A line sequence may be a section of a total line, a conductive path, a line section or the like.

For example, it might be that different conditions regarding the line routing or the structures for generating and/or conducting a signal must be fulfilled at different points of a disposable. Therefore, it may be advantageous to select different technical solutions for the respective line section.

These technical solutions may already be known in detail. In the present invention, they are combined in a favorable manner. In this way, different ranges of requirements (line sequences) may be present within a line section, for which adequate technical solutions (e.g. through-contacting to the sensor, screen printing for the flat connection, 3D and template-free on the multi-connecting device) are selected.

The applied paths/structures have partially different tasks, although they are all in the broadest sense only "paths". Herein, the respective sections are each referred to herein as a line sequence. Thus, for example the first sequence (which itself may again be only a line) may convert a strain into a resistance change, which can be reflected in a signal. This lane is rather thin, meander-shaped flexible and optionally provided on a spatially curved surface. Certain process parameters may basically be intended or provided for this purpose; they may partially be elementary (e.g. the use of ink, the dimension, the strain behavior, the electrical insulation, the shielding (EMC), etc.).

In a second line sequence, only the "transport" or the conducting of signals to a "collection point" (which in turn may be understood as a third line sequence) is concerned. The respective characteristic of the second and third line sequence may be fundamentally different from each other. They do not need to be 3-dimensionally curved anymore and may therefore be applied by screen printing or the like. The same applies for the "collection point". These characteristics are determined by a modified robustness against mechanical contacting (e.g. thicker, stronger . . . ).

A first line sequence, for example, initially represents the converter itself. Here, at a certain point, or in the local environment of a certain point, the parameter to be measured is recorded and converted into an electro-magnetically transferable parameter. This parameter is initially derived from the local environment of the measuring point.

A second line sequence is for example the generally flat line across the medical device, e.g., to the multi connecting device.

A third line sequence is exemplarily the multi connecting device itself and its connection to the machine side. Therefore, a first connection may for example take place between the first line sequence (sensor/converter) and the second line sequence (flat signal line). Thus, a second connection may exemplarily take place between the second line sequence (flat signal line) and the third line sequence (multi connecting device).

In some exemplary embodiments described herein, the application method encompasses or consists of applying conductive ink.

Conductive ink is understood here to mean fluids with nanoparticles or microparticles which, if appropriately tightly applied together, form a functional path such as, e.g., a conductive path (also referred to herein as an electrode) through which, i.a., signals may be transmitted. In the context, materials or aggregate conditions other than conductive ink may also be considered or included. Ideally, conductive ink may be biocompatible; it does not have to be. Additionally or alternatively; living cells, proteins, etc. may be part of the ink rendering it conductive.

The conductive ink or the alternative material may be used in any aggregate conditions. In some embodiments, an aggregate condition may be understood within the context to mean a solid or liquid hydrogel in which a biomarker is incorporated. Frozen (for example, solid) substances or microencapsulated active ingredients/reagents may also be processed. Paths may also be separated from the gas phase by sublimation/condensation.

Conductive ink is here also to be understood as e.g. liquids which comprise carbon-conducting polymers, metal particles and/or combinations thereof, moreover as metalized ink.

The aerosoljet printing technique is considered to be an example for an additive application and, in particular, for printing.

The devices and methods of the present disclosure are of course not limited to the use of the aerosoljet. The person skilled in the art recognizes that all additive and/or template-free printing methods, in particular by which conductive ink may be applied in the sense of this description, are encompassed.

In some exemplary embodiments described herein, an application method encompasses an application in several layers.

In some exemplary embodiments described herein, an application method encompasses a sequence or succession of independent application methods or steps belonging to one and the same application method.

In some exemplary embodiments described herein, the additive application encompasses so-called additive manufacturing or generative production methods.

In particular, the following methods are to be understood herein:
Selective Laser Melting (SLM),
Selective Laser Sintering (SLS),
Selective Heat Sintering (SHS),
Binder Jetting (solidification of powder material by binder)
Electron Beam Melting (EBM)
Fused Deposition Modeling (FDM or Fused Filament Fabrication (FFF)),
application welding or cladding,
Wax Deposition Modeling (WDM),
Contour Crafting,
Metal Powder Application methods (MPA),
Cold Gas Injection
Stereolithography (SLA)+micro-SLA,
Methods using Digital Light Processing (DLP) for exposure to light
Liquid Composite Molding (LCM).
Laminated Object Modeling (LOM),
3D screen printing of metals and
Light-controlled electrophoretic deposition.

In some exemplary embodiments described herein, the application method encompasses, or is, a template-free application. This applies to the first, the second and/or further application methods, or to combinations thereof.

In some exemplary embodiments described herein, a template-free application is to be understood as application without using a mask or template.

In some exemplary embodiments described herein, the application method is no template ink printing, no ink stencil printing, no screen printing, no photo-lithographic process, in particular not in a respective continuous method.

In some exemplary embodiments described herein, a template-free application is to be understood as waiver of any auxiliary layer or bezel which needs to be removed subsequently.

Applying using a template may be understood herein as shadowing or protective shading, in a suitable form, of areas which must not be coated. Such applying takes place, for example, by bezel (e.g. screen printing, spray lacquering etc.) or by lacquer templates (e.g. wafers, printed circuit boards, etc.).

In some exemplary embodiments described herein, the medical device comprises a plurality of converters, for example, two or more, each of which, at least in one section thereof, is directly or indirectly applied to the hard part by an additive application method (or several additive application methods) preferably (a) printing method(s).

In some exemplary embodiments described herein, further sections of a sensor arrangement or of multiple sensor arrangements have been additively applied, preferably by using the same application method.

In some exemplary embodiments described herein, the sections of the one sensor arrangements or of the multiple sensor arrangement which were applied by an additive application method have been applied in the same production step.

In some exemplary embodiments described herein, the sections applied by an additive application method comprise in addition to the at least one converter at least conductive paths, electrodes, a multipole connecting device or respectively several thereof.

In some exemplary embodiments described herein, the converter(s) is/are arranged or configured for measuring or determining the conductivity, concentration, pressure, voltage or current.

In some exemplary embodiments described herein, the application method results in a 2-dimensional or a 3-dimensional application and/or the converters and/or the further sections applied by an additive application method have been applied by the application method 2- or 3-dimensionally.

In some exemplary embodiments described herein, at least one multipole connecting device has also been applied with the first application method or concurrent to the first application method.

In some exemplary embodiments described herein, in addition to the first application method, another application method which is not the second application method has been used for applying the first section, being applied by an additive application method; such a production step may be contemplated by the method.

In some exemplary embodiments described herein, in addition to the second application method, another application method which is not the first application method has been used for applying the second section, being applied by an additive application method; such a production step may be contemplated by the method.

In some exemplary embodiments described herein, the first, second or further sections has been applied, e.g. as two-component printing, e.g. by conductive polymers.

In some exemplary embodiments described herein, the medical device comprises at least one contact pin. The latter is at least partially arranged in the hard part and is in electrical conductive connection with the converter or with a conductive path connected to the converter.

The contact pin may be or may respectively comprise a metal pin or metal section.

The contact pin may be an injection-molded product. It may be produced e.g. by a two-component injection molding. It may comprise e.g. conductive polymers, metallic particles or other electrically conductive materials.

The contact pin may be or may have been applied during the production of the hard part or afterwards.

In some exemplary embodiments described herein, the method further encompasses at least one of the following steps: post-processing steps, in particular performed on the conductive paths or electrodes, as e.g. grinding, polishing, insulating, application of further functional layers of other material; additive application, e.g. by printing, of the signal connection to the machine interface; additive application, e.g. by printing, of the multi connecting device, the combination of two or more sections of the medical device processed by additive application.

The contact pin may be or may have been incorporated into the hard part during the injection molding process with which the hard part has been produced.

In some exemplary embodiments described herein, the medical device is a blood cassette.

It may be provided for a single use during the blood treatment.

In some exemplary embodiments described herein, the method encompasses the application of at least two conductive paths, which cross each other in at least one section. It further encompasses the application of an insulating layer between the conductive paths.

In some exemplary embodiments described herein, the method encompasses the application of a shielding layer to at least one of the conductive paths.

Both the insulating layer and the shielding layer may be applied as conductive paths.

Both the conductive path (also referred to herein as signal conductor) and the multi-connecting device may be applied planarly (for example, 2-dimensionally) or 3-dimensionally with one or several additive and template-free printing techniques. Here, too, one or more post-processing steps, as described above for the conductive path, are optionally encompassed.

In some exemplary embodiments described herein, the method further encompasses combining two or more sections or components of the medical device which were processed by additive application as described herein.

In some exemplary embodiments described herein, the medical device is a tube, tubing system, a tubing set, a blood cassette or a respective part thereof.

A "medical fluid" in the sense of the present disclosure includes each medical liquid and/or each medical gas as well as any combinations. The fluid is preferably blood.

A medical device according to the present disclosure may be a disposable component or a disposable article, which is e.g., made of plastic material.

The medical device according to the present disclosure may be produced by an injection molding process.

The medical device according to the present disclosure may have liquid and/or gas connections, half-open channels and/or chambers. One or more cover elements, such as membranes or foils, may serve to close and/or seal the channels and chambers.

The blood treatment, for which the medical device is used, may, for example, be a dialysis method, a hemodialysis, hemofiltration, hemodiafiltration and the like.

In certain exemplary embodiments described herein, the medical device is a blood cassette. The hard part in such examples is a cassette body or cassette main body or a tube section.

In certain exemplary embodiments described herein, the medical device further comprises at least two connectors for pump tube segments for peristaltic pumps, with or without the pump tube segments.

In certain exemplary embodiments described herein, the medical device has a single-needle sterile membrane.

In certain exemplary embodiments according to the present disclosure, the apparatus comprises strain gauges (DMS sensors). The deformation of the ground results in a change in the length of the measuring path or the conductive sequence and changes their resistance. Alternatively, a material with piezoelectric properties could also be printed, e.g. PVDF (polymer) or piezoceramic. With the aid of the piezoeffect, preferably (fast) pressure changes or vibrations would be measured.

In certain exemplary embodiments according to the present disclosure, the treatment apparatus is a blood treatment apparatus, in particular an apheresis apparatus or dialysis apparatus, in particular a hemofiltration apparatus, a hemodiafiltration apparatus, a filtration apparatus or an apparatus for extracorporeal gas exchange.

In certain exemplary embodiments according to the present disclosure, the treatment apparatus comprises actuators such as e.g. pumps or valves and/or mechanical or non-mechanical interfaces for acting on the medical device through these actuators.

In certain exemplary embodiments according to the present disclosure, the multipole connector of the treatment apparatus comprises a voltage line, by which the medical device is supplied with electrical voltage. The electrical supply may be used for the data read-out as well as for operating the sensors of the medical device.

Examples of converters in the sense of the present disclosure include:
1) Converters for capacitive measurements: A dielectric is placed between two conductive surfaces. The property to be measured has an interaction with the dielectric constant of the dielectric and may be determined by the condenser properties. With this type of converters, the following, amongst others, may be determined: Conductivity, level (filling level or presence of a liquid), pressure, distance (proximity sensor).
2) Converters for resistance measurement: External effects on a wire influences its resistance. With this type of converter, the following, amongst others, may be determined: Temperature, pressure (strain gauges DMS), weight, force, path, contact (yes, no).
3) Converters based on the piezoeffect: A piezodot (e.g. PVDF) is printed on the surface of a measuring cell. Measuring principle based on pressure reception, for example, directly converting the exterior pressure into tension or based on generating ultrasonic (spatial measuring (running time) or density measurements (amplitude) with a second piezodot as receiver in transmission or based on reflection with only one piezodot. With this type of converter, the following, amongst others, may be determined: Air detection, flow measurements, blood detection, spatial measurements (see underwater microphones, screws with applied piezo pressure sensors for tension force monitoring).
4) Magneto-inductive converter: Known disposable MID sensor for measuring flow or conductivity—in this variant, the electrodes are not inserted in the disposable and coated, but printed instead.
5) Optical converters: A reagent is printed onto the measuring surface. It is irradiated either externally or by a likewise printed optical emitter (diode). The properties of the reagent in terms of reflection, absorption, luminescence, fluorescence depend on the parameter to be measured. The information may be obtained by a photodetector, which detects the corresponding intensity. In this, the photodetector may preferably be mounted on the machine side; the converted signal is transmitted via optical conductors to the multi-connecting device and from there to the machine side. With this type of converter, the following, amongst others, may be determined: Discoloration by temperature, pressure, chemical change, pH, pO2, glucose concentration (Hydrogel Optrode).

Some or all of the embodiments of the present disclosure may have one or more of the advantages mentioned above or in the following.

Modern medical systems for blood treatment usually comprise a blood treatment apparatus (on the so-called "machine side") and medical devices (on the so-called "device side") attachable thereto. If the medical device is a disposable, the so-called "disposable side" is also referred to herein. Although the present invention is not limited to disposables, reference is exemplarily made also to disposable medical devices, without being limited thereto. The disposables used for a blood treatment session are discarded for reasons of hygiene after the blood treatment session because they came into, or might have come into, contact with the patients's blood.

In order to monitor the treatment, sensors and actuators, which measure parameters on the disposable article or on the medical device or which act on the latter, are required.

A functionalization of the disposable itself, for example, the integration of all the respective sensors necessary for monitoring a specific parameter in the disposable, has so far been found to be economically unprofitable because the comparatively expensive sensor components would be discarded after each use. Therefore, conventional disposables for medical blood treatment are usually very simple, essentially consisting of the tube for passage or flow of blood. For the above-mentioned reason, they usually do not carry sensors.

These sensors and actuators are consequently provided in the state of the art largely on the machine side. From there, they effect, or are in interaction with, the medical device via a plurality of sensor and/or actuator interfaces. These interfaces generally determine the form factor or design and lead to the fact that medical systems of the prior art cannot be embodied as small as desired.

Some devices as described herein provide cost-effective disposables. Such devices can advantageously allow the miniaturization of the blood treatment systems used and reduce both the extracorporeal blood volume and the effort required for extracorporeal conveyance and hydraulics. The device also, provides effective positioning of sensor components on the medical device and provides a method in which all sensor components arranged on the device side may be integrated in the same production process, which may further reduce the production efforts.

A complete functionalization or only a partial functionalization of the device may reduce the cost per disposable as the device can be discarded together with the converter without significant economic loss due to the particular manner with which the converters are positioned on the device.

For example, with respect to a converter, a partial functionalization is understood to mean that the core task of the converter, for example, detecting a physical, chemical or other parameter or value as well as converting this parameter into an electromagnetically transferrable substitute value, takes place on the medical device itself, either invasively (for example, in contact with blood or a treatment liquid) or non-invasively. However, e.g. the processing of the signals and the interpretation as well as further steps, requiring more sophisticated, e.g. integrated electrical components, is carried out on the machine side. However, in some cases, some or all of the signal processing may also be carried out completely on the machine side. In the latter embodiment of the present disclosure, a complete functionalization is mentioned: at least one sensor arrangement or one sensor, is completely additively applied to the device. In this, the device-side components of a sensor arrangement or of a sensor may be applied according to the present disclosure using the same template-free and additive production method as described supra.

It is also advantageous that disposables disclosed herein, when equipped with individual complete sensors, may thus be fully functionalized. The herein-presented method for applying converters or other components of sensors makes this possible.

The partial functionalization and, hence, the remain of the complex electronics necessary for the post-processing and evaluation of the signals on the machine side is therefore advantageous in that the often simpler-designed components of the respective sensors which are applied by the same additive and template-free printing technology are arranged on the device.

Furthermore, the functionalization is economically advantageous, since the production can be made extremely cost-effective by the common use of the same production technology, for example, in the same production step for all sensor components arranged on the device side.

Since the production method disclosed herein is preferably an additive, template-free printing method, a modified version of the device, e.g., with new sensor geometries, may optionally even be produced by just simply loading or installing the corresponding data record in the software. There is no need to make changes in the production hardware, such as, e.g. the purchase of an injection mold, which would be necessary in the production of the medical device by injection molding. This aspect, too, simplifies the manufacturing and improves the cost-effectiveness.

A further advantage with regard to conventional (non-functionalized) systems described herein is that the physical or chemical parameter to be measured does not need to be guided mechanically to the machine side, as it is the case, e.g., with known pressure sensors within which the pressure conditions to be measured are guided via a pneumatic line to a measuring membrane which is not disposable and is arranged on the machine side. In order to protect the membrane from liquid, complex protective membranes are required regularly, which are referred to as transducer protector (TP). All mechanical interfaces to the machine may thus be omitted. All parameters to be measured may be converted at least into analogue electromagnetic signals (current, voltage, optical signals) by the integrated parts of the sensor system, and may be transmitted only in this form to the processing and evaluation unit on the machine side. For coupling the entire device-side sensor system, only one corresponding multi-channel electromagnetic and/or optical interface is required (multi-connecting device), which allows a significant reduction of the latter.

The devices and methods disclosed herein further allow an optimum transmission of the signals from the converter of the sensors to e.g., a multi-connecting device. This is done by distinguishing different connection or line sequences and the use of the optimum technique for applying the conductive paths with regard to line safety, production speed and costs. Moreover, the present disclosure provides the optimum connection between the single line sequences.

BRIEF DESCRIPTION OF THE FIGURES

In the following, the present invention is described with reference to the accompanying drawings. In the drawings, identical reference numerals denote similar or identical elements. The following applies:

FIG. 5a shows, for example, a machine interface to be connected to the device, here exemplarily designed as a tongs-like or clamp-like connector;

FIG. 5b shows a counterpart of the machine interface of FIG. 5a designed as a planar multipole connecting device;

FIG. 5c shows a counterpart of the machine interface of FIG. 5a designed as a three-dimensional multipole connecting device;

DETAILED DESCRIPTION OF THE FIGURES

Figure 1:
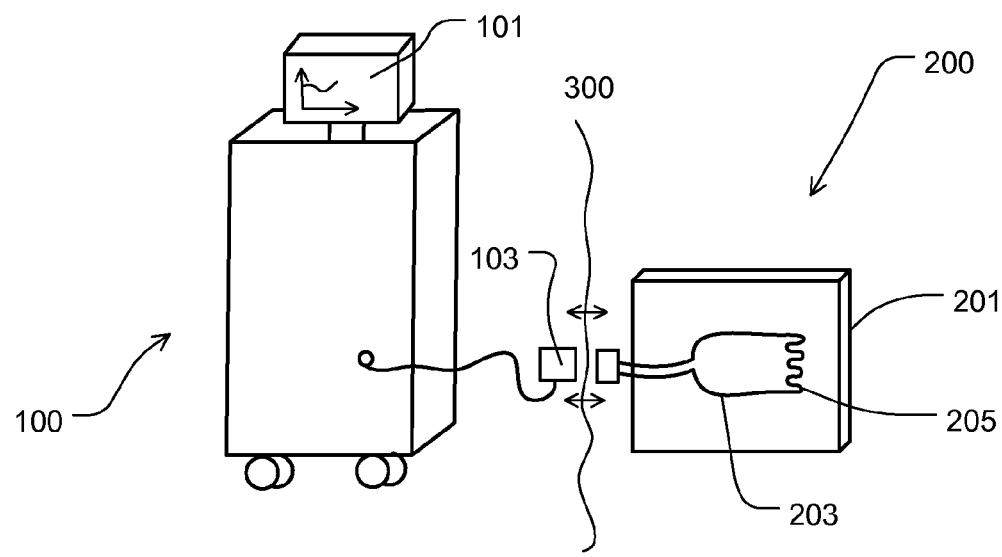
FIG. 1 shows a medical system for blood treatment using a medical device as a partially functionalized disposable.

FIG. 1 shows a very schematic and only exemplary blood treatment apparatus 100 with a medical device 200 (in short: device 200).

The device 200 is exemplarily designed as a disposable. It was partially functionalized by an additive, template-free printing method.

The blood treatment apparatus 100 and the device 200 are connected to each other in signal communication via an interface 300.

The device 200 comprises a hard part 201. Parts of a sensor arrangement, here a conductive path 203 and a converter 205, are provided on the hard part 201.

The conductive path 205 as a whole may be understood to be a first section in the sense which is applied by a first application method.

The conductive path 203 as a whole may be understood to be a second section in the sense which is applied by a second application method.

The converter 205 may be, for example, a pressure sensor. The converter 205 can be printed on the hard part 201. On the disposable side, the converter 205 can only convert the parameter to be measured, here pressure, into an analogue electric signal.

Via the additively printed conductor 203, the electric signal is conducted to the defined interface 300 which is connected to a machine-side evaluation unit indicated by a monitor 101 for displaying the results obtained by the evaluation unit.

On the machine side, the signal can be digitized by an AD (analogue-to-digital) converter or AD converter (short: ADC) 103. Post-processing steps (filtering, smoothing, Fourier transform, zero filling, etc.) may take place prior to a final evaluation and interpretation. All these optional steps can be performed, e.g. in the evaluation unit.

Figure 2:
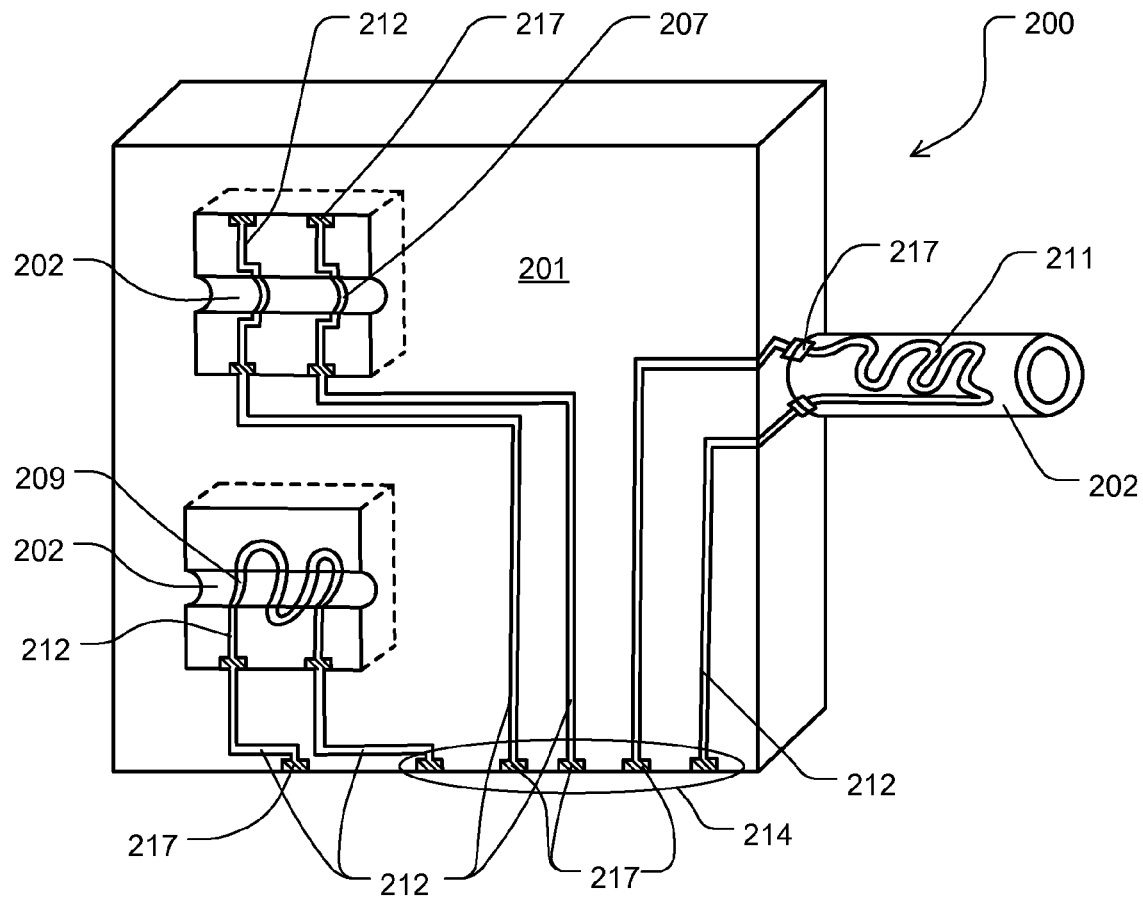
FIG. 2 shows a medical device according to a second exemplary embodiment.

FIG. 2 shows a medical device 200 according to a second exemplary embodiment.

The medical device 200 is a partially functionalized disposable, with three different converters 207, 209, and 211.

FIG. 2, along with the following figures, show each examples of applied converters 207, 209, and 211 and conductive path 212, whereby converter and conductive path were applied by different application methods or by the same application method. Alternatively, at least one of the converters 207, 209, 211 and one of the conductive paths 212, have been each applied by more than one application method—but at least by a first and a second application method.

A converter 207 for measuring the conductivity is exemplarily arranged in the upper left of FIG. 2. In the present simplified representation, the converter 207 consists of two conductive paths which are applied by the additive, template-free printing method, in the interior of a fluid-conducting channel 202 of the device 200.

The two other converters 209, 211 show exemplary embodiments of pressure sensors. These can be arranged as strain gauges on the inner contour (see the converter 209) or on the outer contour (see the converter 211) of the fluid-conducting channel or tube 202 of the device 200.

Besides the converters 209, 211, FIG. 2 shows the electromagnetic signal guide with conductive paths 212 and contacts 217 towards the interface 300, here exemplarily a multipole connecting device 214. The conductive paths 212 towards the signal line may be applied onto the planar surface of the hard part 201 with the same additive and template-free method, in particular in the same production step.

However, non-planar (three-dimensional) line routings or runs, in the sense described supra, or crossings of (correspondingly insulated) lines are possible as well.

The conductive paths 212 and the contacts 217 may be applied by a second likewise additive and template-free printing method, for example, in a second production step, which follows the application of the converters 201, 209, 211. The entirety of the conductive paths 212 used to conduct signals from the location of the respective converter 207, 209, 211, which converts the parameter to be measured, e.g., into an electromagnetic signal, which itself is guided to the machine interface 300 by the conductive paths 212, can also contain individual parts which are applied by a two-component injection molding of conductive polymer.

Figure 3:
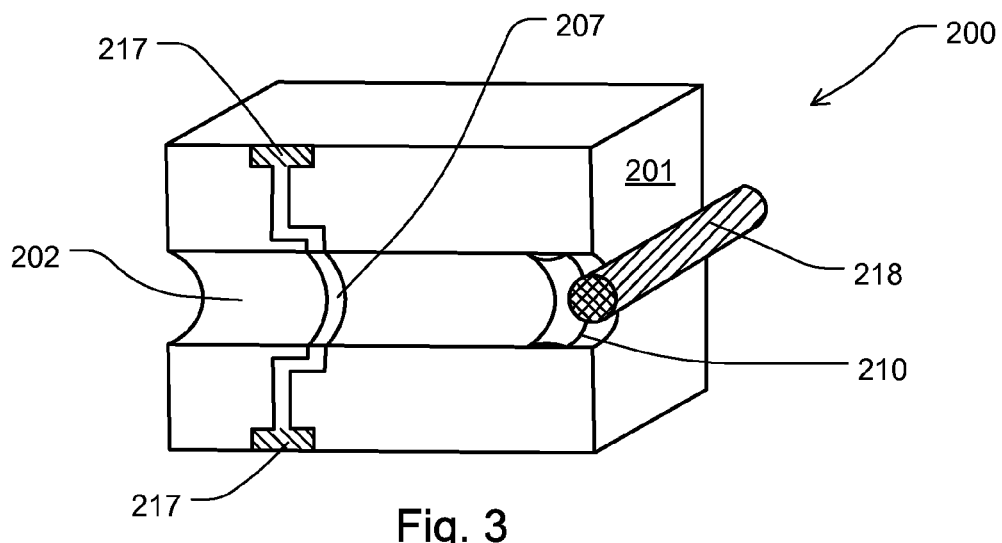
FIG. 3 shows two converters which are applied three-dimensionally by a template-free and additive method along the inner contour of a hard part of a device.

FIG. 3 shows two converters 207, 210. each of which is three-dimensionally applied in the form of a channel in the hard part 201 of the medical device 200 along the inner contour of a fluid path 202 by one or several template-free and additive methods.

The two converters 207, 210 may e.g. be electrodes of a common/shared conductivity sensor. They could also be converters of sensors which measure differently.

FIG. 3 shows two different possibilities of connecting the respective converters 207, 210 respectively their electrodes in a conducting manner—for example—electrically connecting them to a continuing conducting path.

Such a continuing conductive path is typically the flat conductive path of the second line sequence—not shown here. The electrode on the left side is coupled by the same method with which it was also applied on the inner contour of the channel. This may be carried out, for example, by guiding the ends of the electrode over the edge of the channel to the cassette surface when—as shown the channel of the cassette half is open.

In the example on the right side of FIG. 3, the coupling of the converter 210 by a so-called through-connection is shown. For this purpose, a contact pin 218—shown enlarged in FIG. 4—is guided through a section of the hard part 201, e.g. through a blood cassette half. On one side of the hard part 201, the contact pin 218 is conductively connected to the converter 210. On the other side of the hard part 201, the contact pin 218 leads to the flat connection of the second line sequence (not shown here).

In one embodiment, the contact pin 218 may be a metal pin or another metal body which is coated or covered by injection molding during the production of the hard part 201.

The contact pin 218 may alternatively be produced using injection molding, e.g. in a second injection step. In this so-called two-component injection molding, a conductive material, e.g., conductive polymers or compound materials enriched with metallic particles, are used during the injection of the contact pin 218. Finally, the contact pin 218 may also be inserted subsequently into a passage provided for this purpose.

Figure 4:
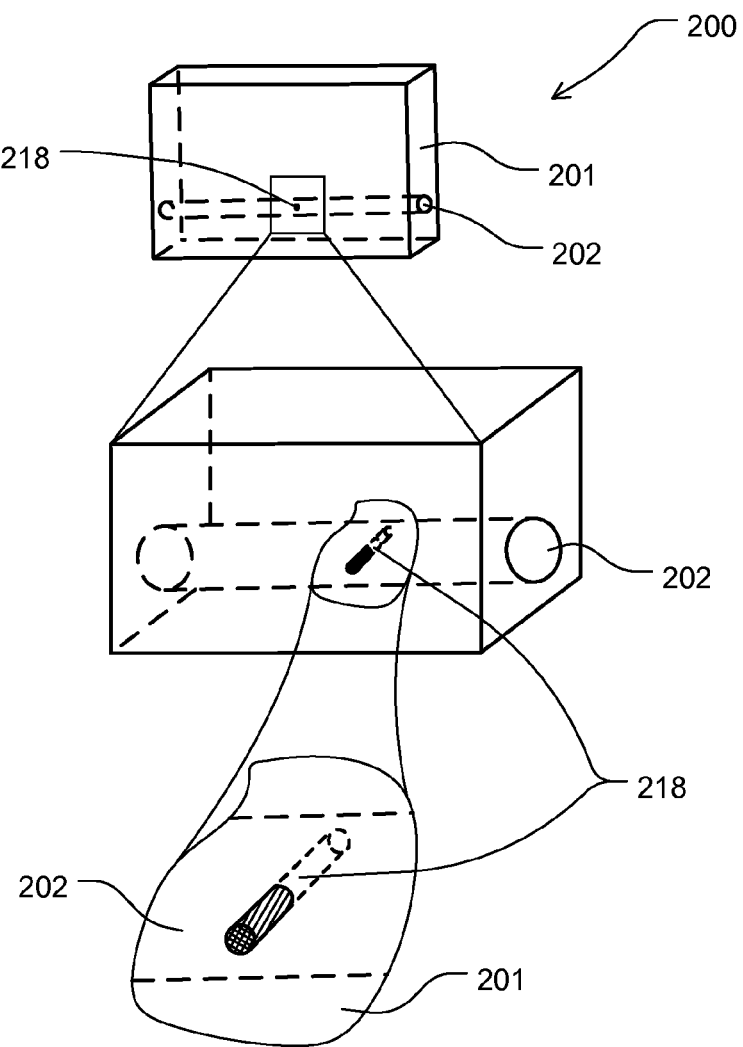
FIG. 4 shows a section of the hard part of the device in a further exemplary embodiment with two enlargements thereof.

FIG. 4 shows the embodiment described herein as a through-connection in several enlargements. It shows the through-connection made possible by e.g. two-component injection molding.

FIG. 5*a* shows the machine interface 300, here designed as a tongs-like or clamp-like connector, in form of tongs 301. The connector, which could also be designed as a plug connector, is embodied to establish a conductive connection to the respective monitoring device or evaluation unit of the blood treatment apparatus 100 (not shown) upon applying or attaching it to the respective contacts of the device 200. For example, analogue, electro-magnetically transferrable signals may be sent from the partially functionalized device 200 to the blood treatment apparatus 100.

FIGS. 5*b* and 5*c* show a counterpart to the tongs 301 of FIG. 5*a* on the side of the device 200 in different views. FIG. 5*b* shows by way of example a flat multipole connecting device 214, for example, the conductive paths 212 are printed exclusively on the surface of the multipole connecting device 214 or of the hard part 201 in the area of the multiple connecting device 214. The multipole connecting device is thus planar printed, for example, 2-dimensionally. The multipole connecting device 214 may be applied by both a template-free, additive method and also classical methods such as screen printing, or the like.

FIG. 5*c* shows the multipole connecting device 214 in an embodiment with three-dimensional printing, for example, the conductive paths are guided around the edge at the end face and also cover (here exemplarily the entire) end face of the section of the hard part 201 which carries the multipole connecting device 214

This embodiment may provide, in particular an improved, contact safety, in the case of mechanically stressed situations where accidental disconnection threatens. The three-dimensional printing of this embodiment is preferably carried out with a template-free, additive method.

The coupling of the multipole connecting device 214 to the second line sequence, for example, the planar connection, which is passed beforehand by the signal from the converter, may be carried out as described above by printing a direct connection. Furthermore, in certain situations, the a.m. coupling by through-connection is also possible.

Figure 6A:
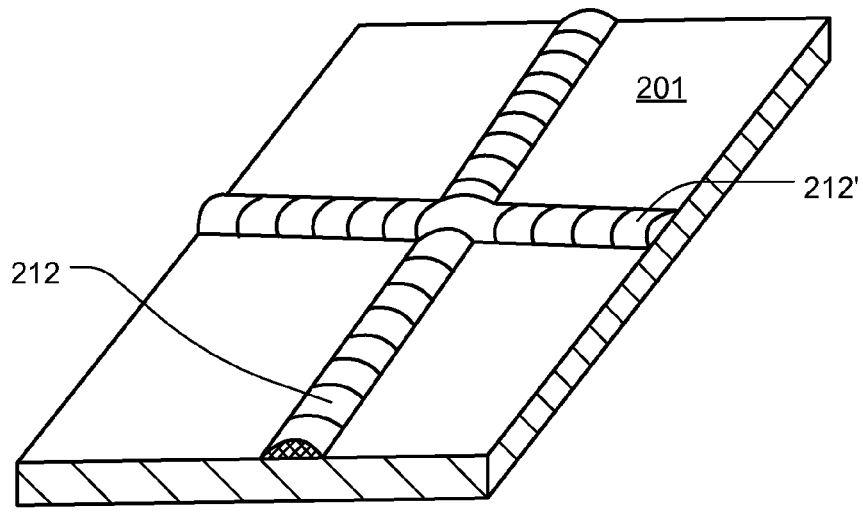
FIG. 6a shows an intersection or an overlapping of two lines of the device.
Figure 6B:
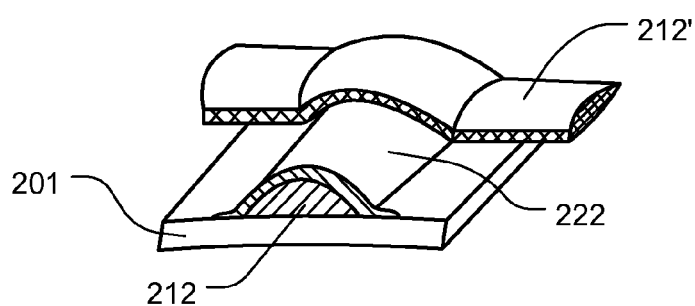
FIG. 6b shows an enlarged section of the illustration of FIG. 6a in section.

FIG. 6*a* and FIG. 6*b* show a further aspect, which is preferably used, e.g. in the a.m. second line sequence and/or with flat conductive paths.

In these connections—herein denoted as planar—the signals of the individual/single converters (not shown in FIG. 6) of the device 200 are guided above or below the surface of the device 200 to the multipole connecting device 214, from where they can be transmitted to the control or evaluation unit of the blood treatment apparatus. Depending on the topology of the surface and the allocation of the individual contacts of the multipole connecting device 214, it may be necessary for individual lines 212, 212' or connections to cross.

Such a crossing or overlapping 220 is shown in FIG. 6a and again in an enlarged section in FIG. 6b.

Such a crossing or overlapping 220 may preferably be provided in, e.g., the a.m. second line sequence and/or with conductive paths. There, it can be implemented with comparatively little effort, since most space is available in the planar connection.

Crossed conductive paths 212, 212' (in short: conductor) are advantageously easy to implement with the method, since they can be produced layer by layer, e.g. using the template-free, additive printing mentioned herein.

In principle, both conductive paths 212, 212' may be applied successively to the surface of the substrate layer. An insulating layer 222 may be applied between the two conductors so that the electromagnetic signals are not interfered by short-circuiting_.

For this purpose, the entire first conductive path 212 may be overprinted or reprinted with an insulating layer 222 so that it is electrically insulated in its whole length against the surface.

Alternatively, the insulation may also be exclusively implemented directly at the point/location of the crossing of the two lines 212, 212'.

If the device 200 is not closed in a later production step through connection with a second device half such as a second cassette half, for example, the second line 212' of the crossing lines lies uncovered, it may also be printed in a second or further printing step with such an insulating layer in order to protect the transmitted signal against short circuits.

In order to further protect the signal against inductive or capacitive couplings through electromagnetic interference signals, a conductive layer (not shown in the figures), which is placed on a shielding potentials, can also be printed around the outer insulating layer.

Alternatively, each of the two crossing lines 212, 212' may also have such a shielding layer outside their insulating layer 222. Each of the shielding layers may be electrically insulated against the outside again by a further insulating layer. This is particularly advantageous in the inner mass layer when the second, crossing conductive path 212' is arranged thereover for signal transport.

LIST OF REFERENCE NUMERALS 100 blood treatment apparatus
101 monitor
103 AD converter
200 blood cassette as an example of a medical device
201 cassette body or cassette main body, hard part; hard body
202 fluid path, channel, flow channel
203 conductive path, conductor or signal conductor
205 converter
207 converter
209 converter
210 converter
211 DMS element as a converter
212 conductive path, conductor or signal conductor
212' conductive path, conductor or signal conductor
214 multipole connecting device, multipole connector
217 contact
218 contact pin
220 crossing or overlapping of conductive paths
222 insulator; insulator layer
300 interface, machine interface

The invention claimed is:

1. A medical device comprising:
    a hard part that is a unitary member defining fluid paths for guiding a medical fluid through the hard part;
    at least one converter, wherein the at least one converter is arranged to measure a characteristic of the medical fluid while the medical fluid is present in one of the fluid paths; and
    a conductive path,
    wherein at least a first section of the at least one converter or of the conductive path is applied to or superimposed directly on the hard part by a first additive application method,
    wherein at least a second section of the at least one converter or of the conductive path is applied directly to the hard part by a second additive application method, and
    wherein the first and the second additive application methods differ from each other.

2. The device according to claim 1, wherein the first additive application method, or the second additive application method, or both the first and second application methods encompass applying conductive ink.

3. The device according to claim 1, wherein the first additive application method, or the second additive application method, or both the first and the second application methods include template-free application.

4. The device according to claim 1, wherein the at least one converter comprises a plurality of converters each comprising at least one section of a first section and a second section, wherein each of the at least one sections are applied to the hard part by an additive application method of a first additive application method and a second additive application method.

5. The device according to claim 4, wherein at least one of the first additive application method or the second additive application method comprises a printing method.

6. The device according to claim 1, further comprising at least one multipole connecting device which has been applied by the first additive application method, the second additive application method, or a third additive application method.

7. The device according to claim 1, wherein the converter is configured to measure or determine conductivity, pressure, tension, or current.

8. The device according to claim 1, wherein the hard part comprises at least one electrically-conducting contact pin, wherein the contact pin is in an electrical conductive connection with the converter or the conductive path.

9. The device according to claim 1, wherein the medical device is a blood cassette.

10. A method for producing a medical device, the method comprising:
    producing or providing a hard part of the medical device, the hard part being a unitary member defining a fluid system for a medical fluid;
    applying at least a first section of a converter or of at least one conductive path directly on the hard part by a first additive application method; and
    applying at least a second section of the converter or of the at least one conductive path directly on the hard part by a second additive application method,
    wherein the first additive application method and the second additive application method differ from each other.

11. The method according to claim 10, wherein applying the first section of the converter or of the conductive path on the hard part by the first additive application method comprises applying conductive ink.

12. The method according to claim 10, wherein applying the second section of the converter or of the conductive path on the hard part by the second additive application method comprises applying conductive ink.

13. The method according to claim 10, wherein the first additive method is a printing method.

14. The method according to claim 13, wherein the first additive application method, or the second additive application method, or both of the first and second additive application methods encompass template-free applications.

15. The method according to claim 10, further comprising applying at least one multipole connecting device by the first additive application method, the second additive application method, or a third additive application method.

16. The method according to claim 10, wherein the method further comprises at least one of the following steps:
 (i) grinding, polishing, insulating, or applying further functional layers of other material on the at least one conductive path;
 (ii) printing a conductor on the device to provide a signal connection from the medical device to a machine;
 (iii) printing a multipole connecting device on the medical device; and
 (iv) combining at least two sections of the medical device which were applied by an additive application.

17. The method according to claim 10, further comprising:
 molding the hard part of the medical device using an injection molding process; and
 applying a contact pin into the hard part of the medical device.

18. The method according to claim 10, further comprising:
 molding the hard part of the medical device using an injection molding process, wherein molding the hard part of the medical device comprises applying a contact pin into the hard part of the medical device.

19. The method according to claim 10, wherein the at least one conductive path comprises at least two conductive paths which cross in at least one section, the method further comprising:
 applying an insulating layer between the at least two conductive paths.

20. The method according to claim 19, further comprising:
 applying a shielding layer on at least one of the at least two conductive paths.

* * * * *